US00PP28881P2

(12) United States Plant Patent
Ault

(10) Patent No.: US PP28,881 P2
(45) Date of Patent: Jan. 16, 2018

(54) ***PHLOX* PLANT NAMED 'PINK PARASOL'**

(50) Latin Name: ***Phlox borealis*×*Phlox bifida***
Varietal Denomination: Pink Parasol

(71) Applicant: James Robert Ault, Libertyville, IL (US)

(72) Inventor: James Robert Ault, Libertyville, IL (US)

(73) Assignee: CHICAGO LAND GROWS, INC, Glencoe, IL (US)

( * ) Notice: Subject to any disclaimer, the term of this patent is extended or adjusted under 35 U.S.C. 154(b) by 100 days.

(21) Appl. No.: 14/998,560

(22) Filed: Jan. 19, 2016

(51) Int. Cl.
*A01H 5/02* (2006.01)

(52) U.S. Cl.
USPC ..... Plt./320

(58) Field of Classification Search
USPC ..... Plt./320
See application file for complete search history.

(56) References Cited

PUBLICATIONS

Trademark hit on 'Pink Parasols', Serial No. 78384522, published Dec. 7, 2004.*

* cited by examiner

*Primary Examiner* — Anne Grunberg
(74) *Attorney, Agent, or Firm* — Penny J. Aguirre

(57) ABSTRACT

A new cultivar of *Phlox* plant named, 'Pink Parasol', that is characterized by its flower petals that are distinctly bifid with a deep cleft, its flowers that have a distinct center eye that is white in color and remains persistent for the life of the flower, its striae that are inconspicuous and if visible form 2 indistinct narrow dark violet lines at the base of each petal lobe, its flowers that are medium purplish pink in color with the pigments persisting or darkening slightly as the flowers age, its flowers that cover 90% to 100% of the plant at peak bloom, and its broad mounding habit that does not spread into an indeterminate groundcover like most moss *phlox*.

2 Drawing Sheets

Botanical classification: *Phlox borealis*×*Phlox bifida*.
Cultivar designation: 'Pink Parasol'.

BACKGROUND OF THE INVENTION

The present invention relates to a new and distinct cultivar of *Phlox* plant, botanically an interspecific hybrid known as *Phlox* 'Pink Parasol' and will be referred to hereafter by its cultivar name, 'Pink Parasol'. The new cultivar represents a new moss *phlox*, a herbaceous perennial grown for landscape use.

The new invention arose from an ongoing controlled breeding program by the Inventor in Glencoe, Ill. The objectives of the breeding program are to develop improved cultivars of interspecific hybrids of *Phlox* with novel ornamental traits such as unique flower colors, plant habits, flower fragrance and adaptability to garden conditions in the upper Midwest (U.S.D.A. Zone 5) and similar climates.

'Pink Parasol' was derived from a cross made in April of 2006 under controlled conditions (that excluded natural pollinators) between an unnamed and unpatented plant of *Phlox borealis* as the female parent and an unnamed plant of *Phlox bifida* as the male parent. The resulting seedlings were planted for evaluation in June of 2007. 'Pink Parasol' was selected in May of 2008 as a single unique plant amongst the resulting seedlings.

Asexual propagation of the new cultivar was first accomplished by shoot tip cuttings by the Inventor in June of 2008 in Glencoe, Ill. Asexual propagation by shoot tip cuttings has determined that the characteristics of this cultivar are stable and reproduced true to type in successive generations

SUMMARY OF THE INVENTION

The following traits have been repeatedly observed and represent the characteristics of the new cultivar. These attributes in combination distinguish 'Pink Parasol' as a unique cultivar of *Phlox*.

1. 'Pink Parasol' exhibits flower petals that are distinctly bifid with a deep cleft.
2. 'Pink Parasol' exhibits flowers that have a distinct center eye that is white in color and remains persistent for the life of the flower.
3. 'Pink Parasol' exhibits petal striae that are inconspicuous and if visible form 2 indistinct narrow dark violet lines at the base of each petal lobe.
4. 'Pink Parasol' exhibits flowers that are medium purplish pink in color with the pigments persisting or darkening slightly as the flowers age.
5. 'Pink Parasol' exhibits flowers that cover 90% to 100% of the plant at peak bloom.
6. 'Pink Parasol' exhibits a broad mounding habit that does not spread into an indeterminate groundcover like most moss *phlox*.

The female parent of 'Pink Parasol', an unnamed plant of *Phlox borealis*, differs from 'Pink Parasol' in having a petals with a cleft that is less deep in size, striae that are conspicuous, broad and red-violet in color, in having flowers that produce a faint white eye at the base of the petal lobes that disappears as the flower matures and in having a plant habit that forms a spreading mat with a shorter plant height. The male parent of 'Pink Parasol', an unnamed plant of *Phlox bifida*, differs from 'Pink Parasol' in having petal lobes that are much narrower in size, in having petal bases that do not overlap, in having striae that are dark violet in color, distinct, and longer and broader in size, in lacking a center eye, and in having a low, small, open mounding plant habit, and having 50% less flower coverage at peak bloom. 'Pink Parasol' can also be most closely compared to the *Phlox subulata* cultivars 'Fort Hill' (not patented) and 'Blue Hills' (not patented). 'Fort Hill' is similar to 'Pink Parasol' in flower color and in having bifid petal lobes with a distinctly shaped cleft. 'Fort Hill' differs from 'Pink Parasol' in having striae that are distinct, broad and deep red-purple in color, in having a petal base that is solid in color or has in indistinct white colored eye that disappears as the flower matures, in having a broad, mat-forming plant habit that forms a broad groundcover, and in having a re-blooming habit in autumn. 'Blue Hills' is similar to 'Pink Parasol' in having flowers with bifid petal lobes and a distinct cleft and in having the same blooming period. 'Blue Hills' differs from 'Pink Parasol' in having flowers that are larger in size and reddish violet in color that age to a lighter bluish violet color with irregular pigmentation on the petal lobes, in having leaves that lack ciliated margins, and in having a mat-forming plant habit that forms a broad groundcover.

BRIEF DESCRIPTION OF THE DRAWINGS

The accompanying colored photographs illustrate the overall appearance and distinct characteristics of the new *Phlox* as grown in Glencoe, Ill.

The photograph in FIG. 1 provides a view of a plant 2 years in age of 'Pink Parasol' in bloom as grown in a one-gallon rootmaker container.

Figure 1:
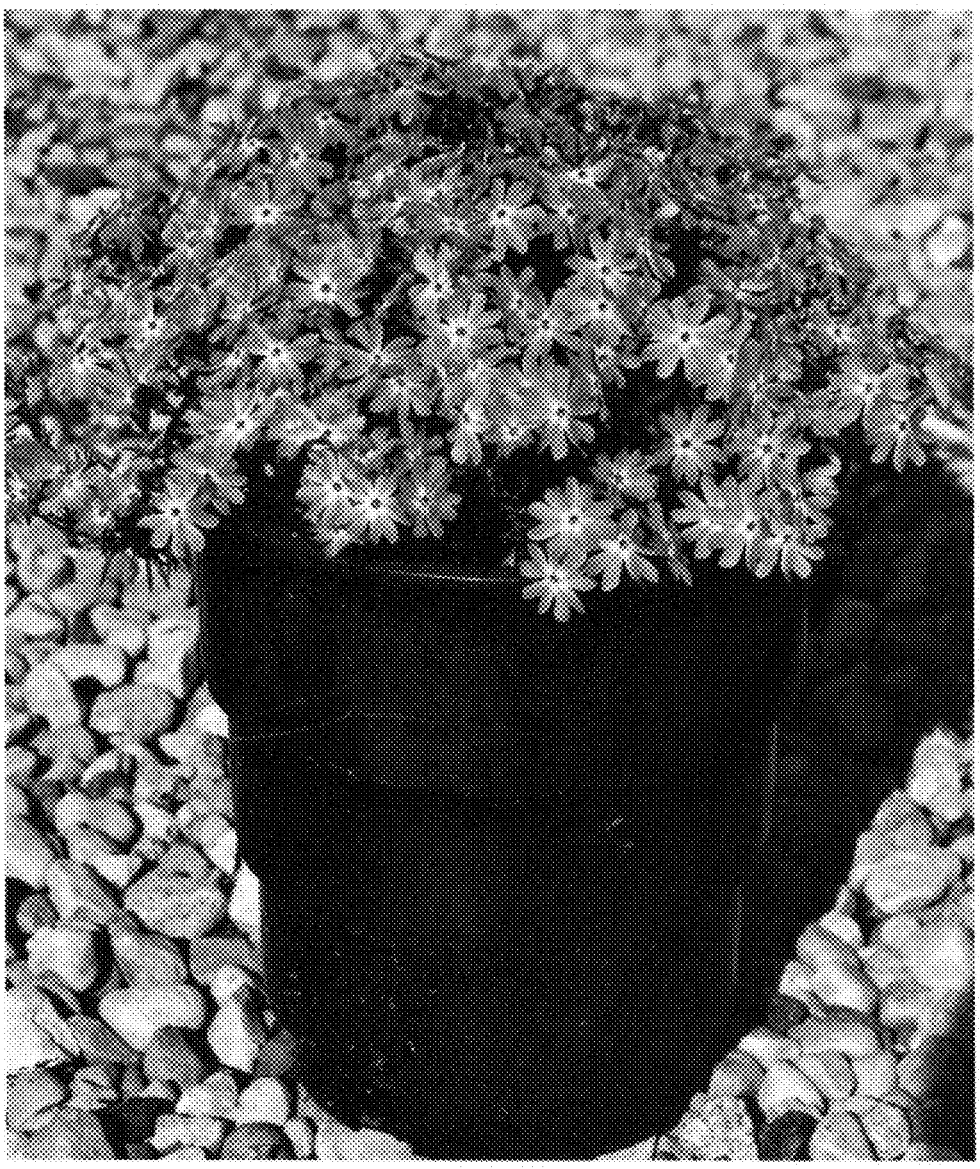
Figure 2:
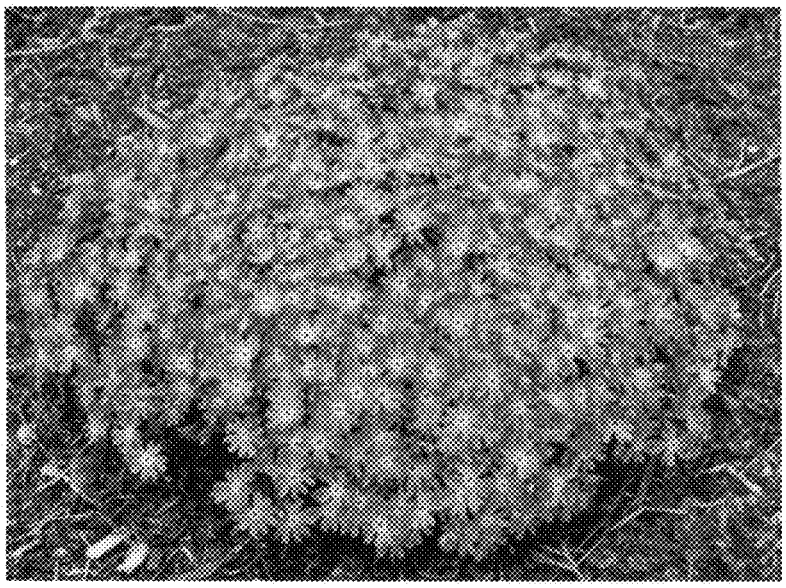

The photographs in FIG. 1 and FIG. 2 were taken of a plant 2 years in age as grown in a trial garden.

The photograph in FIG. 2 provides a view of the plant habit of 'Pink Parasol' in bloom.

Figure 3:
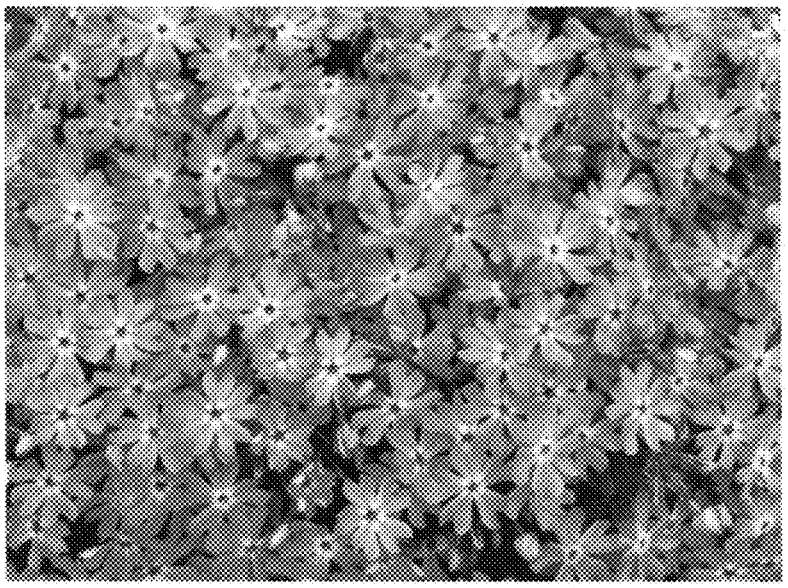

The photograph in FIG. 3 provides a close-up view of the inflorescences of 'Pink Parasol'.

The colors in the photographs are as close as possible with the photographic and printing technology utilized and the color values cited in the Detailed Botanical Description accurately describe the colors of the new *Phlox*.

DETAILED BOTANICAL DESCRIPTION OF THE PLANT

The following is a detailed description of nine month-old plants of the new cultivar as grown in 4-inch containers in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms for four weeks from late April to late May in northern Illinois.

*Plant habit.*—Broad mounding habit that does not spread into an indeterminate groundcover like most moss *phlox*.

*Height and spread.*—In-ground trial plants 2 years in age; average of 30 cm in width and 12 cm in height at peak bloom, in-ground trail plants 5 years in age; average of 51 cm in width and 17 cm in height at peak bloom.

*Hardiness.*—At least hardy in U.S.D.A. Zones 4 to 8.

*Diseases and pests.*—Very good resistance to powdery mildew (caused by *Erysiphe cichoracearum*) has been observed.

*Root description.*—Fibrous.

*Root development.*—Shoot tip cutting will root under mist in 4 to 5 weeks in late spring to early summer, rooted cutting will fully root in a 2.5 inch pot in about 3 months and when tranplanted in fall and overwintered in a 4-inch pot, they will bloom the following spring.

*Growth rate.*—Relatively vigorous for a moss *phlox*.

*Propagation.*—Shoot tip cuttings.

Stem description:

*Stem size.*—An average of 6.5 cm in length and 1.5 mm in width.

*Stem shape.*—Rounded.

*Stem strength.*—Strong and flexible.

*Stem color.*—139C to 139D suffused with 183B.

*Stem surface.*—Smooth, very slightly glossy, and densely covered with wooly hairs about 1 mm in length.

*Stem aspect.*—Held upright.

*Internode length.*—An average of 1.5 cm.

*Branching habit.*—Well branched, an average of 10 lateral stems per main stem.

Foliage description:

*Leaf shape.*—Lanceolate to linear.

*Leaf division.*—Simple.

*Leaf base.*—Truncate to cuneate.

*Leaf apex.*—Aristulate.

*Leaf venation.*—Pinnate, inconspicuous, matches leaf color on upper and lower surfaces.

*Leaf margins.*—Entire and ciliate with fine hairs an average of 1 mm in length.

*Leaf attachment.*—Sessile.

*Leaf arrangement.*—Opposite.

*Leaf surface.*—Smooth, shiny, and sparsely covered with fine hairs an average of 1 mm in length on upper and lower surfaces.

*Leaf color.*—Upper surface; 137A and lower surface; 137C.

*Leaf size.*—An average of 1.5 cm in length and 3.5 mm in width.

*Leaf quantity.*—An average of 12 leaves (6 pairs) per stem.

*Leaf fragrance.*—Slight grassy scent.

Flower description:

*Inflorescence type.*—Panicle on terminus of lateral branches.

*Lastingness of inflorescence.*—About 3 to 4 weeks from the opening of the first flower to senescence of last flower, individual flower lasts about 5 days.

*Inflorescence size.*—An average of 2.5 cm in height and 5 cm in diameter.

*Flower fragrance.*—Moderate floral scent.

*Flower number.*—An average of 3 per inflorescence.

*Flower aspect.*—Upright and outward.

*Flower bud.*—Spatulate in shape with acute apex, an average of 1.2 cm in length and up to 3 mm in width, color; petal portion a blend of N74D and 75D and calyx portion; 157A with striations 90B.

*Flower form.*—Salverform.

*Flower size.*—An average of 7 mm in height and 2 cm in diameter.

*Corolla tube.*—An average of 1.1 cm in length and 2 mm in width, color; a blend between 157D and 92A, glabrous and satiny surface.

*Corolla lobes.*—5, obcordate in shape, held nearly horizontally when fully open, slightly overlapping near base, an average of 1 cm in length and 9 mm in width, bifid with a deep cleft, apex of lobes rounded, base broadly cuneate and fused to tube, entire margins, color; upper surface when opening; N74C to N74D with eye N155A and a faint pair of narrow striae 93A near base, lower surface when opening; N81A to N81D, upper surface when fully open; N88B to N88D with eye N155A and faint pair of narrow striae 93A near base, lower surface when fully open; 92A to 92D, color fades to N89C to N89D with eye persistent, glabrous and satiny upper and lower surfaces.

*Calyx.*—Campanulate in form, comprised of fused sepals with linear shaped sepal tips free, an average of 8 cm in length and 1.2 mm in width.

*Sepals.*—5, primarily fused with free tips, linear in shape, entire margins, fused base (about 80%), aristulate apex, an average of 7 mm in length and 1 mm in width, inner surface; glabrous, smooth, and shiny, outer surface; moderately covered with wooly hairs about 1 mm in length, color on inner and outer surface; a blend between 137A and 138A.

*Peduncles.*—Rounded in shape, an average of 2.5 cm in length and 1 mm in width, held upright to outward, color; 144A to 144B, surface; smooth, dull, and densely covered with wooly hairs about 0.5 mm in length.

*Pedicels.*—Rounded in shape, an average of 1.5 cm in length and 0.8 mm in width, held at an average angle of 7° to peduncle, color; 144A to 144B heavily suffused with 183B; smooth, slightly glossy, and densely covered with wooly hairs about 0.5 mm in length.

Reproductive organs:

*Gynoecium.*—1 pistil, stigma; tri-lobed, each lobe is about 1 mm in length and 13B in color, style; about 1.1 cm in length and 0.2 mm in width, 149D in color, ovary; superior, ovate to oval in shape, about 1 mm in length and width, 143A in color.

*Androcoecium.*—5 stamens, anthers; dorsifixed, oblong in shape, 1 mm in length, and 17A in color, filaments; adnate to petals, an average of 6 mm in length and 155C in color, pollen is abundant in quantity and 17A in color.

*Seeds.*—None observed.

It is claimed:

1. A new and distinct cultivar of *Phlox* plant named 'Pink Parasol' as herein illustrated and described.

* * * * *